United States Patent
Wang et al.

(10) Patent No.: US 11,118,150 B2
(45) Date of Patent: Sep. 14, 2021

(54) LAYERED MICROFLUIDIC ARRAY

(71) Applicants: Research Foundation of the City University of New York, New York, NY (US); Memorial Sloan Kettering Cancer Center, New York, NY (US)

(72) Inventors: Sihong Wang, Scarsdale, NY (US); A. H. Rezwanuddin Ahmed, New York, NY (US); Xuejun Jiang, Cresskill, NJ (US); Chun-wei Chi, New York, NY (US); Chenghai Li, New York, NY (US)

(73) Assignees: Research Foundation of the City University of New York, New York, NY (US); Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 16/244,797

(22) Filed: Jan. 10, 2019

(65) Prior Publication Data
US 2019/0161715 A1    May 30, 2019

Related U.S. Application Data

(63) Continuation-in-part of application No. 15/231,101, filed on Aug. 8, 2016, now abandoned, which is a
(Continued)

(51) Int. Cl.
*C12M 3/00* (2006.01)
*B01L 3/00* (2006.01)
(Continued)

(52) U.S. Cl.
CPC ....... *C12M 23/16* (2013.01); *B01L 3/502715* (2013.01); *B01L 3/502746* (2013.01);
(Continued)

(58) Field of Classification Search
CPC ....... B01L 2300/0864; B01L 2300/087; B01L 2300/0874; B01L 3/502746; B01L 3/502761; B01L 2200/0668
See application file for complete search history.

(56) References Cited

U.S. PATENT DOCUMENTS

| 7,736,050 B2 | 6/2010 | Park et al. |
| 2002/0187560 A1 | 12/2002 | Pezzuto et al. |

(Continued)

FOREIGN PATENT DOCUMENTS

| CN | 101649290 | 5/2012 |
| WO | WO2001019505 | 3/2001 |

(Continued)

OTHER PUBLICATIONS

Wang W.-X. et al. "Construction of Tumor Tissue Microarray on a Microfluidic Chip," Chin J Anal Chem, May 2015, 43(5), 637-642 (Year: 2015).*

(Continued)

*Primary Examiner* — Christopher Adam Hixson
*Assistant Examiner* — Michelle Adams
(74) *Attorney, Agent, or Firm* — Peter J. Mikesell; Schmeiser, Olsen & Watts, LLP

(57) ABSTRACT

A layered, microfluidic array is disclosed. The array has a first layer with a culture channels extending in a first longitudinal direction. Each culture channel includes multiple traps that entrap cell or tissue samples. The array also has a second layer with microfluidic channels extending in a second longitudinal direction that is orthogonal the first longitudinal direction. A third layer, disposed between the first layer and the second layer, has pores arranged within the third layer such that each nest is vertically stacked above, and fluidly connected with, a corresponding culture chamber in the first layer. Each nest is fluidly isolated from adjacent
(Continued)

nests by a fluid impermeable region of the third layer such that horizontal diffusion of water within the third layer is prevented.

18 Claims, 14 Drawing Sheets

Related U.S. Application Data continuation-in-part of application No. 14/257,182, filed on Apr. 21, 2014, now Pat. No. 10,144,945, which is a continuation of application No. PCT/US2012/061229, filed on Oct. 20, 2010.

(60) Provisional application No. 62/202,503, filed on Aug. 7, 2015, provisional application No. 61/549,322, filed on Oct. 20, 2011.

(51) Int. Cl.
    *C12M 3/06*     (2006.01)
    *C12M 1/00*     (2006.01)

(52) U.S. Cl.
    CPC ....... *B01L 3/502761* (2013.01); *C12M 23/22* (2013.01); *B01L 2200/0668* (2013.01); *B01L 2300/087* (2013.01); *B01L 2300/0816* (2013.01); *B01L 2300/0819* (2013.01); *B01L 2300/0874* (2013.01); *B01L 2300/0887* (2013.01); *B01L 2300/168* (2013.01)

(56) References Cited

U.S. PATENT DOCUMENTS

| | | | |
|---|---|---|---|
| 2010/0006479 A1* | 1/2010 | Reichenbach | G01N 15/1056 209/132 |
| 2010/0120077 A1 | 5/2010 | Daridon | |
| 2010/0163109 A1* | 7/2010 | Fraden | B01L 3/50273 137/1 |
| 2010/0323447 A1 | 12/2010 | Takayama et al. | |
| 2011/0004304 A1 | 1/2011 | Tao et al. | |
| 2011/0082563 A1 | 4/2011 | Charest et al. | |
| 2014/0228250 A1 | 8/2014 | Wang et al. | |
| 2014/0273223 A1 | 9/2014 | Cho et al. | |

FOREIGN PATENT DOCUMENTS

| | | |
|---|---|---|
| WO | WO2010013016 | 2/2010 |
| WO | WO2011014674 | 2/2011 |

OTHER PUBLICATIONS

International Search Authority (ISA/US); International Search Report dated Jan. 18, 2013 for PCT/US12/61229, 2 pgs.

Zhang et al.; Self-Complementary Oligopeptide Matrices support mammalian cell attachment; Biomaterials 16 (1995) pp. 1385-1393 (total 8 pgs.).

Zhang et al.; Spontaneous assembly of a self-complementary oligopeptide to form a stable microscopic membrane; Proc. Natl. Acad. Sci USA, vol. 90, Apr. 1993; pp. 3334-3338 (total 5 pgs.).

King et al.; A high-throughput microfluidic real-time gene expression living cell array; Lab Chip; Jan. 2007; 7(1): pp. 77-85 (total 9 pgs.).

Gurski et al.; 3D Matrices for Anti-Cancer Drug Testing and Development; Oncology Issues Jan./Feb. 2010, pp. 20-25 (total 6 pgs.).

Dereli-Korkut, Z. et al.; Three Dimensional Microfluidic Cell Arrays for ex Vivo Drug Screening with Mimicked Vascular Flow; Analytical Chemistry; Feb. 25, 2014; pp. 2997-3004; vol. 89; 2014 American Chemical Society.

Liu, M. et al.; A 3-D microfluidic combinatorial cell array; Biomed Microdevices; Nov. 10, 2010; pp. 191-201; 13, Springer.

* cited by examiner

LAYERED MICROFLUIDIC ARRAY

CROSS-REFERENCE TO RELATED APPLICATIONS

This application is a continuation-in-part of U.S. patent application Ser. No. 15/231,101 (filed Aug. 8, 2016) which claims priority to U.S. patent application 62/202,503 (filed Aug. 7, 2015) and is also a continuation-in-part of U.S. patent application Ser. No. 14/257,182 (filed Apr. 21, 2014) which is a continuation of international application PCT/US2012/061229 (filed Oct. 20, 2012) which claims priority to U.S. provisional patent application 61/549,322 (filed Oct. 20, 2011). The content of each of the aforementioned applications is hereby incorporated by reference in its entirety.

STATEMENT REGARDING FEDERALLY FUNDED RESEARCH OR DEVELOPMENT

This invention was made with government support under contract no. U54CA137788-01 awarded by the National Institute of Health (NIH) and under contract nos. 1055608 and 1343051 awarded by the National Science Foundation (NSF). The government has certain rights in the invention.

FIELD OF THE INVENTION

This invention relates, in one embodiment, to a three dimensional microfluidic cell array or microfluidic tissue array that functions as a scaffold for growing cells or tissues.

BACKGROUND

The promise of improved cancer therapy has been one of the driving forces for cell death research over the past decade. There is growing evidence that many of the molecular and cellular changes that occur in cancer development diminish the ability of cells to undergo apoptosis and that resistance to apoptosis causes drug resistance. On the other hand, many studies have demonstrated that apoptosis is a frequent outcome of effective anticancer therapy. Therefore, developing and screening novel anticancer drugs that target apoptosis pathways have received increasing attention in the past few years. Identification of novel compounds and drug targets involved in apoptosis regulation is still a major roadblock to anticancer drug development due to the lack of a high throughput apoptotic screening system which can systematically measure dynamic expression of multiple proteins and genes as well as enzyme activities in real time in intact cells from multiple stimuli.

Cell cultures are often grown in the lab to assist in measuring the effectiveness of an anticancer drug. For example, colonies of cancer cells can be grown from cells that were removed from a patient. A variety of drugs may be tested for activity against these particular cancer cells. Conventionally, these colonies are grown in suspension or in two-dimensional arrays. This environment does not adequately mimic the native environment of the cancer cell when it was within the patient. This environmental change can impose phenotypic changes in the resulting colony of cancer cells that may, in some instances, alter the responsiveness of the colony to anti-cancer agents.

Some attempts have been made to produce three-dimensional cell arrays but these have not proven entirely satisfactory. Therefore, an improved device and method for growing cells is desired.

SUMMARY OF THE INVENTION

In a first embodiment, a layered, microfluidic array is provided. The layered, microfluidic array comprising: a first layer comprising a plurality of culture channels extending in a first longitudinal direction, each culture channel having a width and a plurality of traps, each trap comprising (1) a curved path and (2) a culture chamber, each culture chamber comprising a fluid diverter that diverts fluid into a bypass opening and a flow-through opening, the bypass opening uniting with the culture channel at a unification opening, the flow-through opening have a diameter between 10% and 50% of the width; a second layer comprising a plurality of microfluidic channels extending in a second longitudinal direction, wherein the first longitudinal direction and the second longitudinal direction are orthogonal; a third layer, disposed between the first layer and the second layer, the third layer comprising pores grouped into a plurality of nests, each nest horizontally arranged within the third layer such that each nest is vertically stacked above, and fluidly connected with, a corresponding culture chamber in the first layer, each nest fluidly isolated from adjacent nests by a fluid impermeable region of the third layer such that horizontal diffusion of water within the third layer is prevented; a fluid inlet connected to a first end of the microfluidic channel; a fluid outlet connected to a second end of the microfluidic channel.

An advantage that may be realized in the practice of some disclosed embodiments of the cell array is that the native environment experienced by a cell is more closely approximated.

BRIEF DESCRIPTION OF THE DRAWINGS

The present invention is disclosed with reference to the accompanying drawings, wherein:

FIG. 3A is a bisected profile of an exemplary cell array showing fluid flow paths while

Corresponding reference characters indicate corresponding parts throughout the several views. The examples set out herein illustrate several embodiments of the invention but should not be construed as limiting the scope of the invention in any manner.

DETAILED DESCRIPTION

Figure 1:
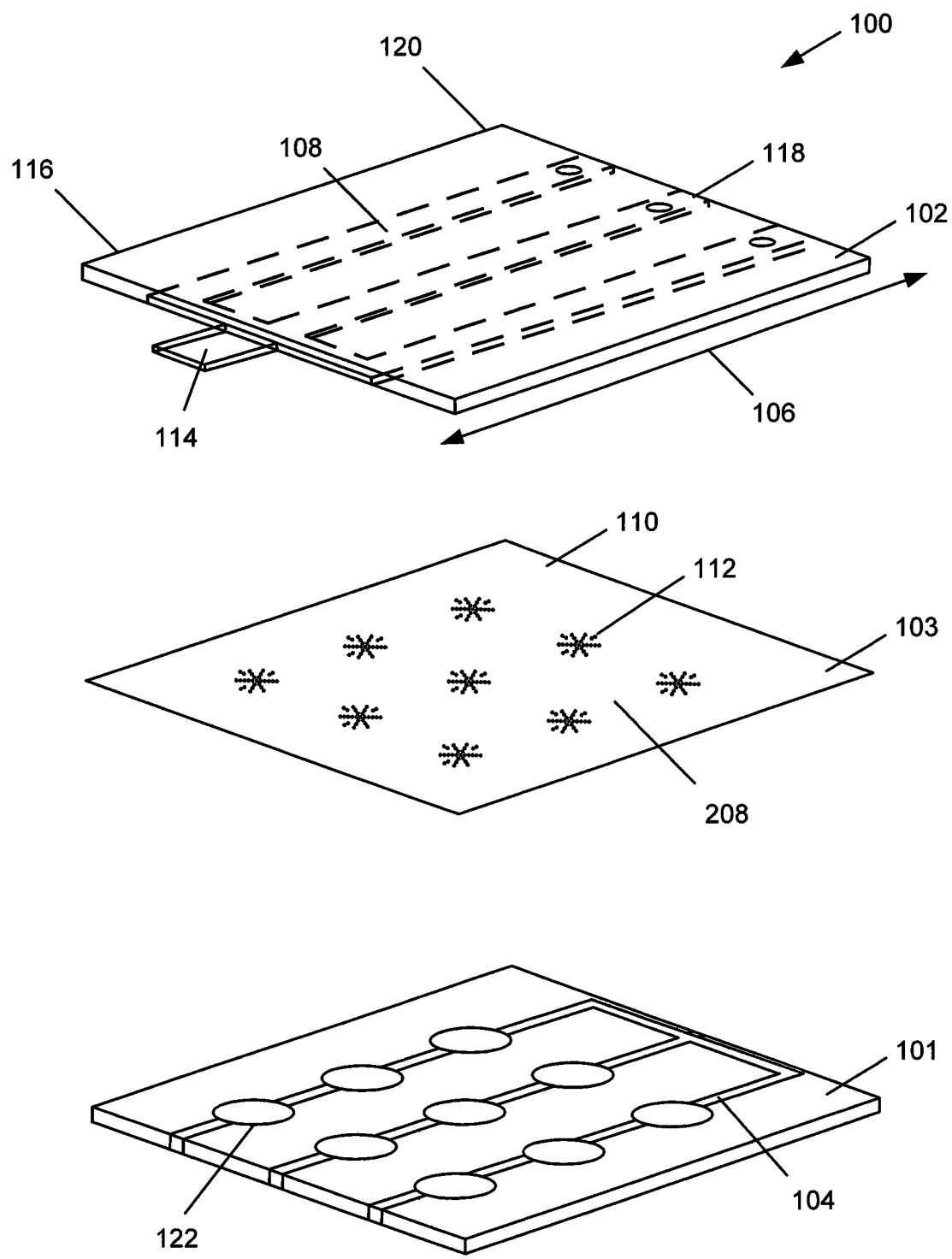
FIG. 1 is an exploded view of an exemplary cell array.

FIG. 1, is an exploded view of an exemplary layered three-dimensional (3D) microfluidic living cell array 100.

The cell arrays disclosed in this specification are useful both for cell culturing as well as tissue culturing. The cell array 100 provides a nanoscaffold hydrogel that permits cells, such as cloned cancer cells, tissues or nonmalignant cells, to grow in a synthetic three-dimensional matrix. Cell array 100 comprises a first layer 101, a second layer 102 and a third layer 103 that is disposed between the first layer 101 and the second layer 102. The first layer 101, the second layer 102 and the third layer 103 are stacked together and integrated into a single cell array 100. Both the first layer 101 and the second layer 102 are contiguous with the third layer 103. In the embodiment depicted, the third layer 103 is in contact with both the first layer 101 and the second layer 102. The first layer 101 comprises a plurality of cell culture channels 104 which, in the exemplary embodiment, includes a plurality of cell culture chambers 122. The third layer 103 comprises a membrane 110 with a nest (i.e. group) of pores 112 that fluidly connect a cell culture channel 104 to a microfluidic channel 108 of the second layer 102. Each nest in the nest of pores 112 is separated from adjacent nests by fluid impermeable regions 208 which serve to fluidly isolate each nest from adjacent nests such that horizontal diffusion of water-based fluids within the third layer is prevented. This is a significant advantage over many conventional arrays which permit fluid diffusion through the third layer. By preventing diffusion through the third layer, cross contamination between different microfluidic channels is prevented. This is particularly useful in combinatorial drug screening processes (see, for example, FIG. 10).

The microfluidic channel 108 extends along longitudinal direction 106. The microfluidic channel 108 comprises a fluid inlet 114 at a first end 116 of the second layer 102 and a fluid outlet 118 at a second end 120 of the second layer 102. The first end 116 and the second end 120 are disposed on opposite ends of the second layer 102 and are spaced apart along longitudinal direction 106. The fluid inlet 114 may be connected to, for example, a syringe pump for delivering fluids at a predetermined flow rate. The flow rate may be selected to approximate the flow rate of blood through a small blood vessel. In one embodiment, the flow velocity is between 500-1000 microns per second. In another embodiment, the flow rate is between 100-800 microns per second. In yet another embodiment the flow rate is between 100-200 microns per second. The flow rate is the product of the flow velocity multiplied by the cross-sectional area of the channel.

Figure 2:
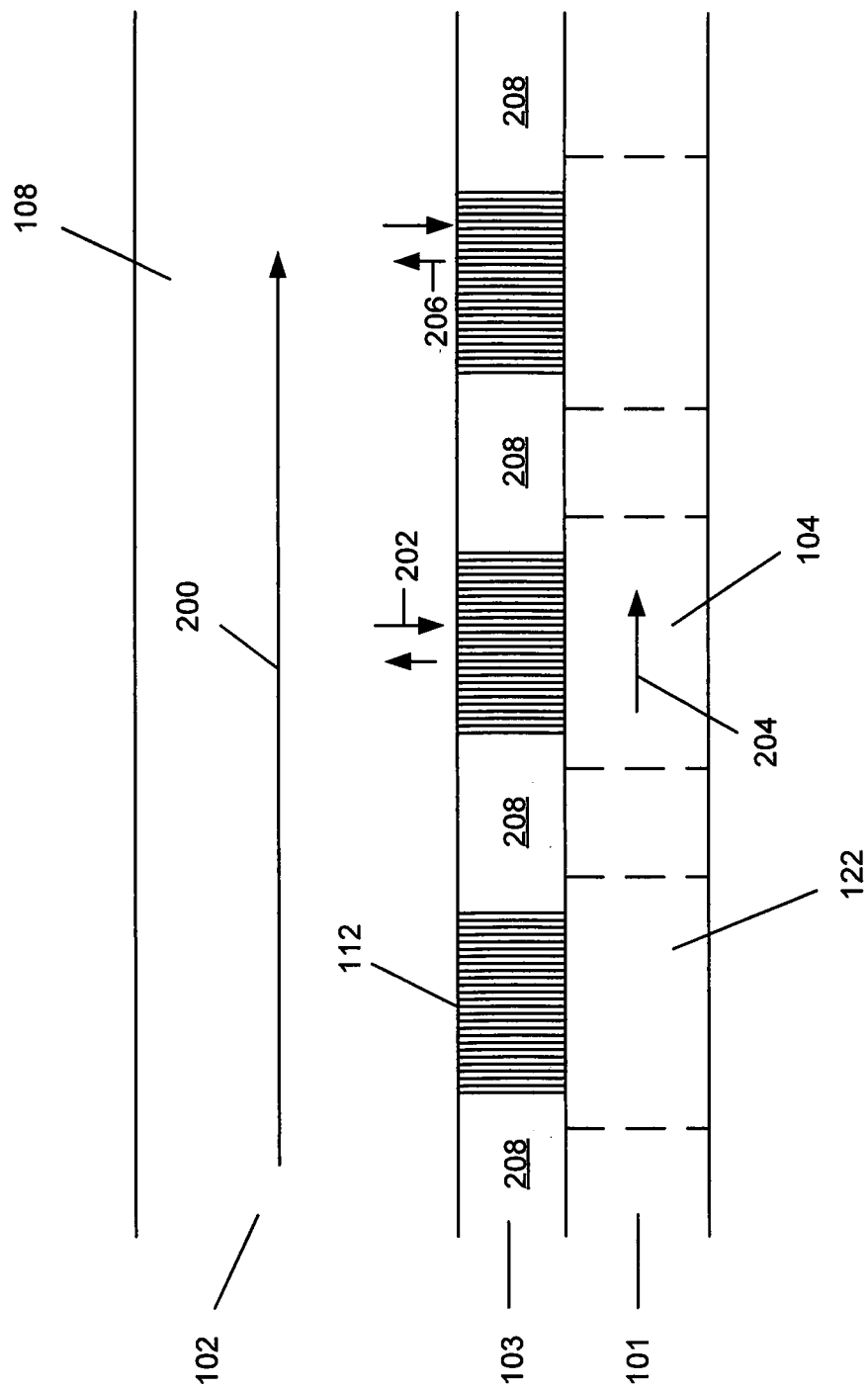
FIG. 2 is a bisected profile of an exemplary cell array.

Referring to FIG. 2, during operation cells are introduced into the cell culture channels 104 (e.g. introduced into the cell culture chambers 122). The cell culture channels 104 may be filled with a suitable media, such as a hydrogel media. The media provides a porous environment suitable for growing cells. Nutrients are dissolved or suspended in a liquid and introduced into the fluid inlet 114 at a predetermined rate. The fluid flows in direction of arrow 200 until it exits the fluid outlet 118. The flow rate through microfluidic channel 108 flows at a relatively high rate, compared to the very low flow rate through the second layer 102 and the low flow rate in the third layer 103. Advantageously this minimizes the shear stress cells experience in the cell array to more closely approximate an in vivo environment.

As shown in FIG. 2, a nest of pores 112 fluidly connect the microfluidic channel 108 to the cell culture channels 104. In the embodiment depicted, each of nest of pores 112 are horizontally arranged within the third layer 103 such that each nest is vertically stacked above a corresponding cell culture chamber 122 of the cell culture channel 104. Each nest is vertically stacked above the cull culture chambers such that the pores are within a circumference defined the corresponding cell culture chamber. Each nest is spaced from adjacent nests by the fluid impermeable region 208. Nutrients in the fluid pass into the cell culture channels 104 in the direction of arrow 202, limited by the size of the pores within the nest of pores 112. This is generally a diffusion-controlled process. Once the nutrients pass into the cell culture channels 104 they are transported in the direction of arrow 204. Other material, such as the waste products of the cells and excess nutrients, diffuse in the direction of arrow 206 where they rejoin the fluid in the microfluidic channel 108. These other materials are transported in the direction of arrow 200 where they exit cell array 100 at fluid outlet 118.

Figure 3A:
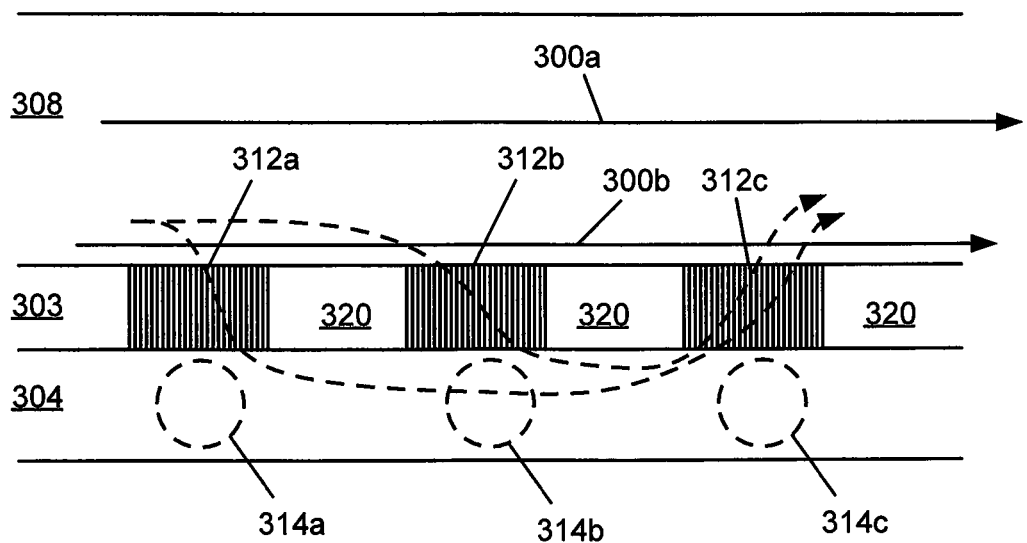

The microfluidic dynamics of cell array 100 provides a three dimensional environment that closely approximates the environment experienced by a cell in its native (biological) environment. By mimicking the fluid dynamics provided by arteriole, venule and capillary systems, cells grown within the cell array 100 can be grown in a fashion that more closely matches native growth patterns. This makes it more likely the cloned cells will retain the biological characteristics (e.g. drug susceptibility) of the cells, leading to more accurate drug screening tests. FIG. 3A provides another view of the microfluidic dynamics of cell array 100.

FIG. 3A shows a microfluidic channel 308, a third layer 303 with pores 312a, 312b and 312c separated by fluid impermeable regions 320. A cell culture channel 304 is also depicted. Fluid flows quickly through the microfluidic channel 308 in the direction of arrow 300a. Due to fluid dynamics, the flow rate of the fluid proximate the walls of the microfluidic channel 308 is slower. See arrow 300b. A portion of the fluid passes through nest of pores 312a, 312b and 312c, into the cell culture channel 304 and exits the pores to rejoin the microfluidic channel 308. Fluid dynamic calculations indicate the flow rate in the cell culture channel 304 is, in one embodiment, about 0.1 micrometers per second, which corresponds to the interstitial flow rate in vivo. Wherein a cell culture channel, flow rate through the nest of pores 312a (the upstream pore) is relatively fast. Likewise, the flow rate through nest of pores 312c (the downstream pore) is also relatively fast. The flow rate through nest of pores 312b, which is between the upstream and downstream pore, is somewhat slower. The flow rate gradually changes with the nest of pores at the center of the third layer 303 having the slowest flow rate. The flow rate through the nest of pores increases as one moves either upstream or downstream relative to the central nest.

The flow rate through the cell culture channel 304 is generally fastest at point 314b which is at the center of the cell culture channel 304. The flow rates through cell culture channel 304 decreases as one moves either upstream or downstream from the center of the cell culture channel 304. For example, fluid dynamic calculations show the flow rates at points 314a and 314b are relatively slow. The fluid dynamic behavior results in a subtle concentration gradient of material within the fluid. Examples of two such gradients are shown in FIG. 3B.

Figure 3B:
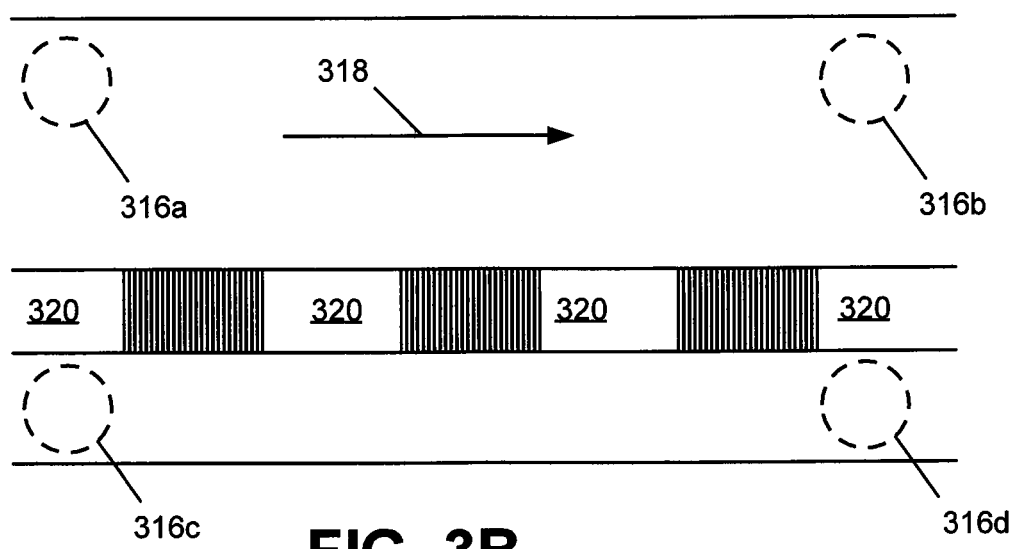
FIG. 3B is a bisected profile of an exemplary cell array showing concentration gradients.

FIG. 3B schematically depicts the subtle concentration gradients for a nutrient (oxygen) and a waste product (carbon dioxide). The subtle concentration gradient confirms that the cell array can efficiently perform oxygen delivery and carbon dioxide removal even with subtle concentration gradients. The concentration of oxygen is relatively high at point 316a. As the fluid flows in the direction of arrow 318, a portion of the oxygen migrates through the pores and is consumed by the cells. The concentration of oxygen at point 316b is therefore lower than point 316a. Modeling suggests the concentration gradient in the microchambers is present, but subtle (e.g. about 0.0003%) and that the vertical concentration gradient between the first layer and the second layer is sufficient for efficiency oxygen/carbon dioxide exchange. The lowest concentration of oxygen is at point 316d. The concentration of oxygen at point 316c is similar to that of point 316b, due to a balancing of diffusion and flow rate. In a similar fashion, the concentration of carbon dioxide follows the same trend with the opposite direction. Carbon dioxide concentration is relatively low at point 316a. As the fluid flows in the direction of arrow 318, a portion of the carbon dioxide migrates from the cells through the pores and joins the fluid. The concentration of carbon dioxide at point 316b is therefore higher than point 316a. The highest concentration of carbon dioxide is at point 316d. The concentration of carbon dioxide at point 316c is similar to that of point 316b, due to a balancing of diffusion and flow rate.

Figure 4:
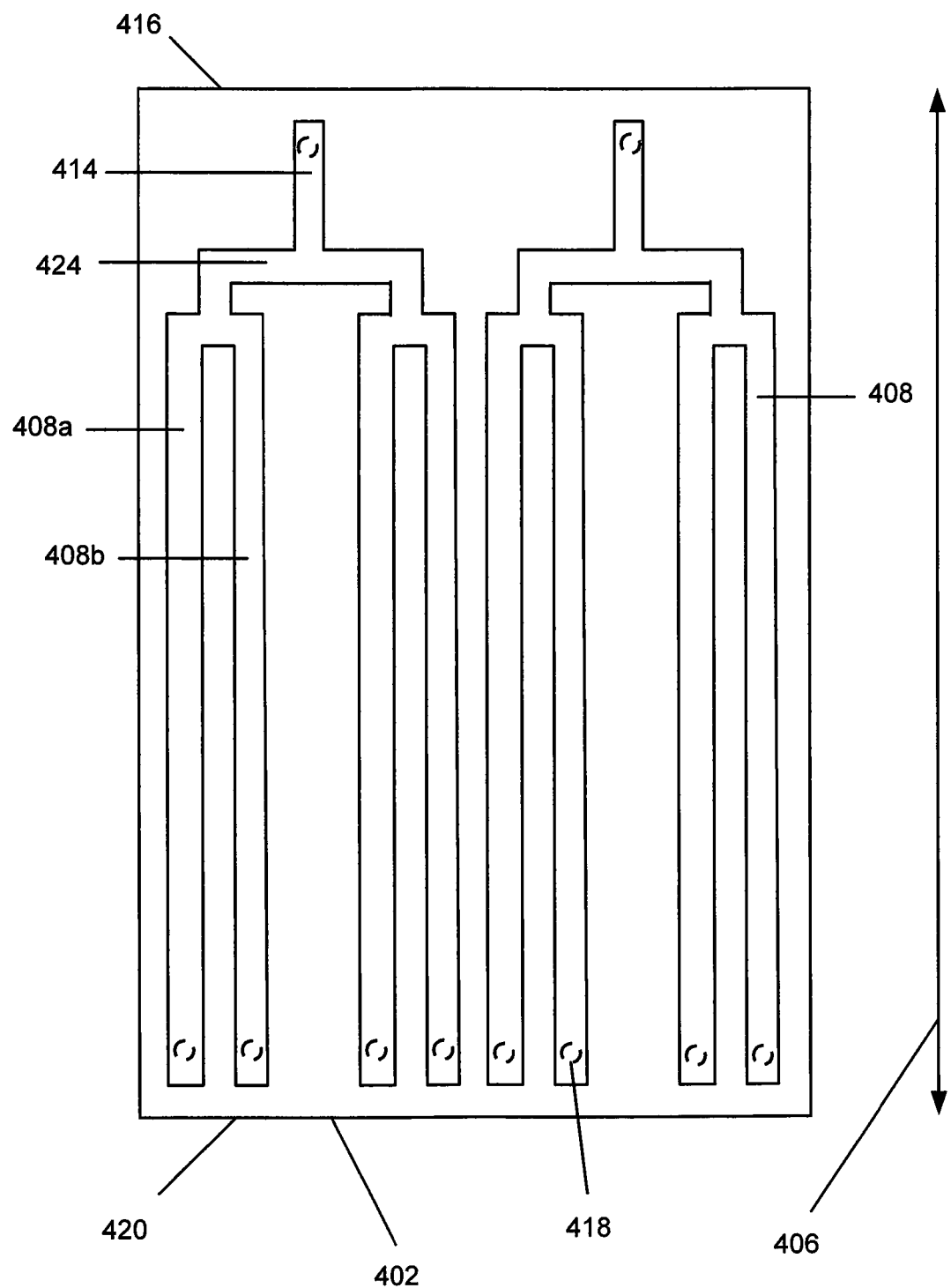
FIG. 4 is a schematic view of an exemplary second layer.

FIG. 4 is a detailed top view of an exemplary second layer 402. The second layer 402 is formed of an optically transparent material to facilitate viewing of the cellular samples as well as probing of the samples using microscopic techniques. The second layer 402 comprises a plurality of microfluidic channels 408 including a first microfluidic channel 408a and a second microfluidic channel 408b. The channels extend in a longitudinal direction 406. The first microfluidic channel 408a and the second microfluidic channel 408b are fluidly connected by a joining channel 424 at a first end 416 which is opposite second end 420. When fluid is introduced to fluid inlet 414, the fluid flows through joining channel 424 and into the first microfluidic channel 408a and the second microfluidic channel 408b. Excess fluid exits through fluid outlet 418. The microfluidic channels 408 are vertically stacked above the pores of the third layer 503. See FIG. 5.

Figure 5:
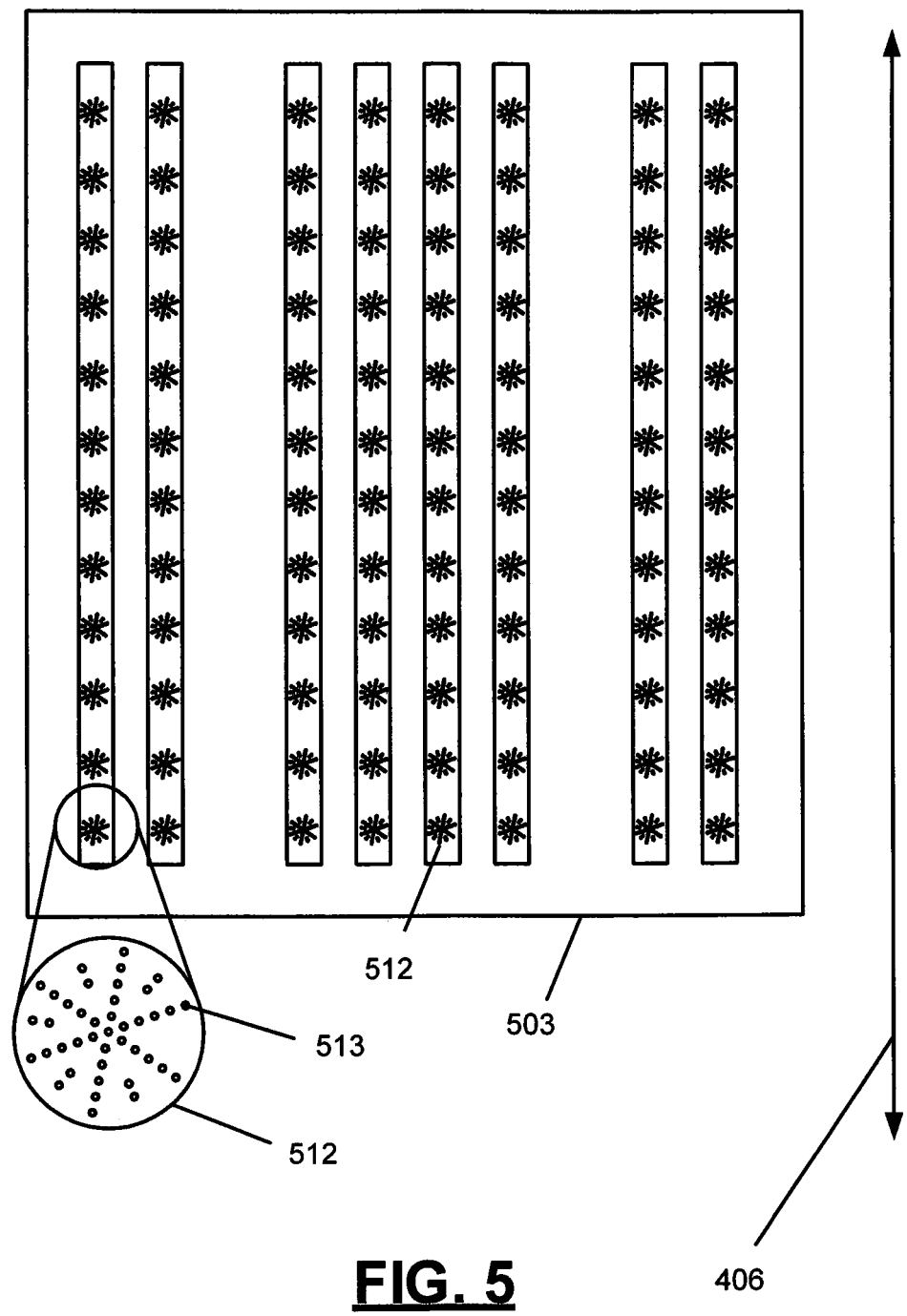
FIG. 5 is a schematic view of an exemplary third layer.

FIG. 5 is a depiction of an exemplary third layer 503. The third layer 503 is formed of an optically transparent material. In the embodiment of FIG. 5, the pores 513 are grouped into nests of pores 512. The pores 513 have a diameter suitable to control the rate of diffusion of material through the pores. The pores 513 may have a diameter of between about 10 micrometers and about 40 micrometers. For example, in one embodiment the pores 513 have a diameter of about 20 micrometers. The nests of pores 512 are arranged in a line that extends along longitudinal direction 406 so as to vertically stack the pores 513 with the microfluidic channels 408 and fluidly connect them. The nests of pores 512 are also arranged to be vertically stacked above corresponding cell culture chambers. In one embodiment, there is one nest of pores 512 for each cell culture chamber (i.e. a one-to-one ratio).

Figure 6:
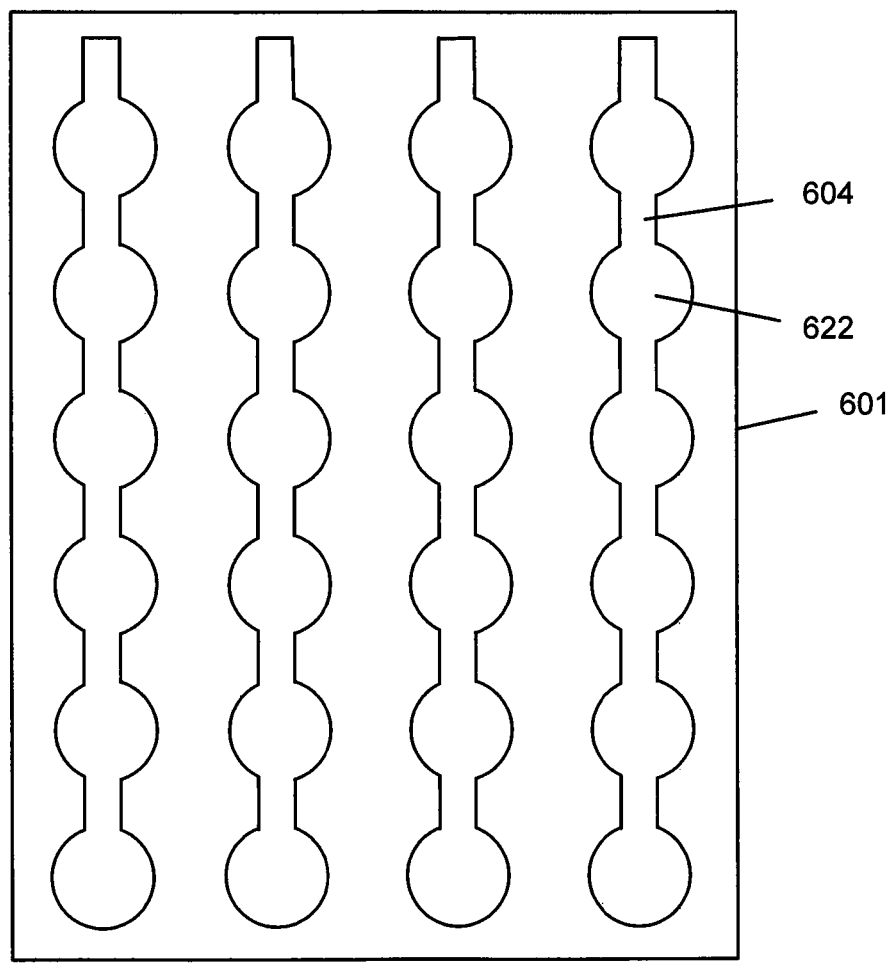
FIG. 6 is a schematic view of an exemplary first layer.
Figure 7:
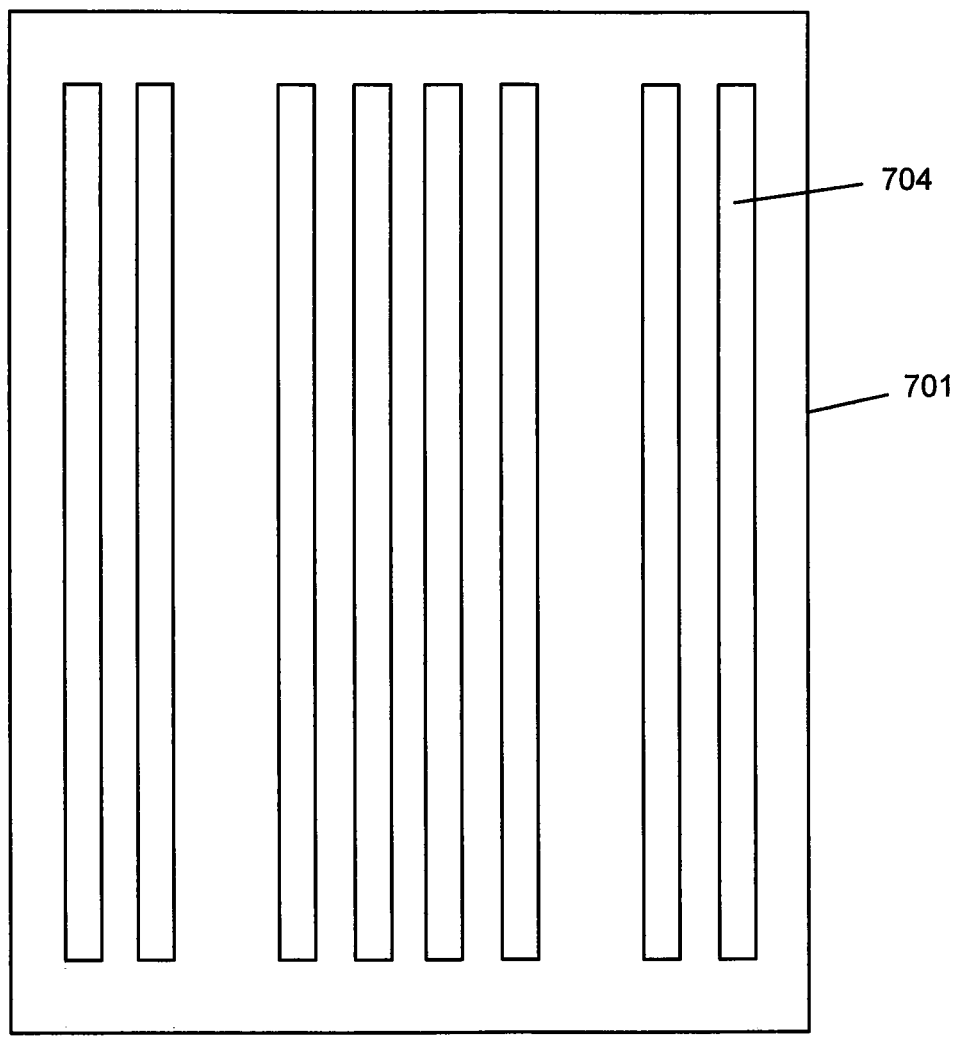
FIG. 7 is a schematic view of an exemplary first layer.

FIG. 6 is a top view of an exemplary first layer 601. The first layer 601 is formed of an optically transparent material. The first layer 601 comprises a plurality of cell culture chambers 622 joined by cell culture channels 604. In the embodiment depicted there are twenty-four cell culture chambers 622 in a 4×6 array of cell culture chambers. Such an embodiment may be used with a third layer that has twenty-four nests of pores, each of which is vertically stacked above a corresponding cell culture chamber. A wide variety of cell culture chamber configurations may be used. For example, an 8×8 array of cell culture chambers may be used. In another embodiment, a 10×10 array is used. The aforementioned arrays and merely examples. The cell array is highly scalable for use in high throughput drug screen in a clinical or industrial setting. In those depicted embodiments where cell culture chambers are used, the chambers are circles with a diameter greater than the width of the cell culture channels. In one embodiment, the cell culture chambers are circles with a diameter between about 100 micrometers and about 800 micrometers. In one embodiment, the cell culture chambers are circles with a diameter of about 770 micrometers. The width of the cell culture channels and the microfluidic channels corresponds to the width of blood vessels and is generally several hundred micrometers. This precise width may be adjusted depending on what types of blood vessels are being mimicked. In one embodiment, the width of the channels is between 50 microns and 500 microns. In another embodiment, shown in FIG. 7, the first layer 701 comprises a plurality of cell culture channels 704 that do not include designated cell culture chambers 122. Cellular growth occurs within cell culture channels 704.

Figure 8:
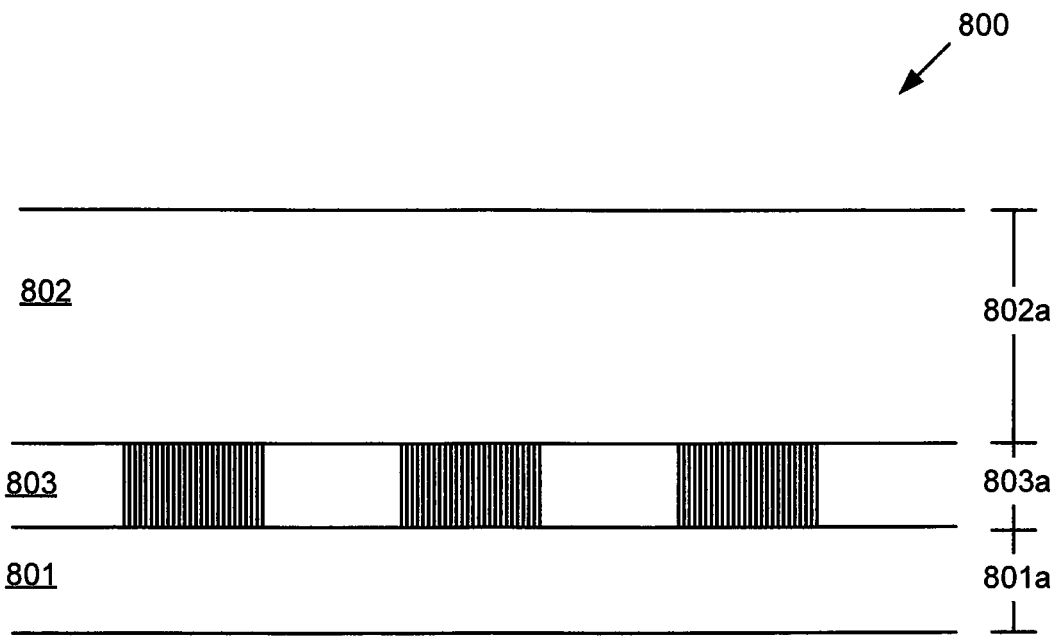
FIG. 8 is a bisected profile of an exemplary cell array.
Figure 9:
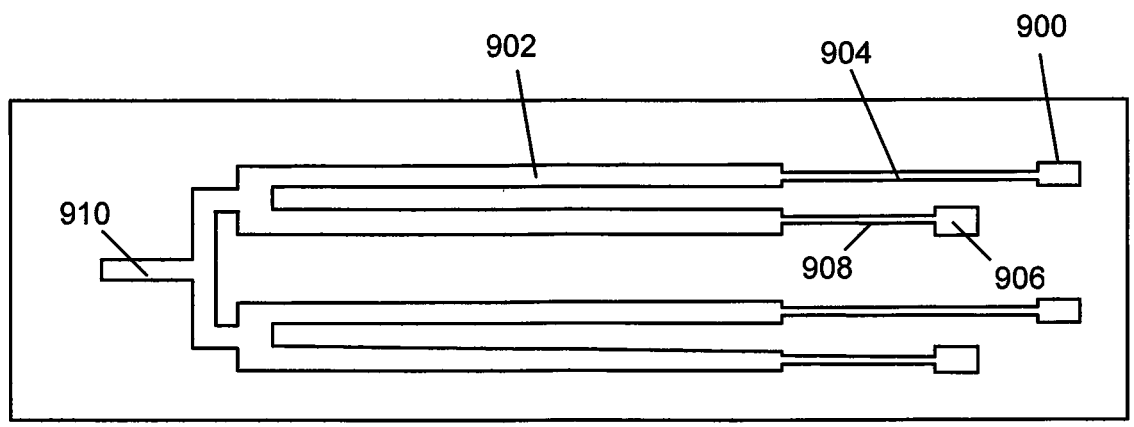
FIG. 9 is a schematic view of a channel with access ports.

FIG. 8 is a bisected side view of an exemplary cell array 800 comprising first layer 801, second layer 802 and third layer 803. The first layer 801 has a first thickness 801a. The second layer 802 has a second thickness 802b. The third layer 803 has a third thickness 803a. In the embodiment depicted, the first thickness 801a is greater than the third thickness 803a but is less than the second thickness 802a. In one embodiment, the first thickness 801a and second thicknesses 802a are both greater than the third thickness 803a. In one embodiment, the first thickness 801a is between 60 and 100 micrometers. In another embodiment, the first thickness 801a is between 70 and 90 micrometers. In one embodiment, the second thickness 802a is about 130 micrometers, the third thickness 803a is about 40 micrometers and the first thickness 801a is about 80 micrometers. By providing a relatively thick second layer 802, a desirable flow rate is maintained. By controlling the thickness of third layer 803, the diffusion rate can be controlled. The thickness of the first layer 801 provides a three-dimensional volume within which cells can be grown. The relative thickness of first layer 801 impacts the microfluidics of the cell array. In one embodiment, the first thickness and second thickness are between 60 micrometers and 1 millimeter each.

In some embodiments, a first access port 900 is disposed at a terminus of a channel 902 that connects the channel 902 to the ambient environment. Fluid, which may contain samples, may be withdrawn through these access ports. Channel 902 may be a cell culture channel of the first layer or a microfluidic channel of the second layer. In those embodiments where the channel 902 is a microfluidic channel of the second layer, the access port can function as a fluid outlet where excess liquid is expelled. In those embodiments where the channel 902 is a cell culture channel, the access port can be used to selectively withdraw samples for subsequent testing. To access the content of channel 902, one can form (as by drilling) a hole in the layer. Since the first access port 900 has a relatively large area, it is easier to properly position the hole than it would be were first access port 900 small. This is particularly advantageous considering the small size of many of the exemplary arrays. To avoid inadvertently drilling into channel 902, the first access port 900 is spaced from the channel 902 by a path 904 that fluidly connects the access port 900 to the channel 902. To minimize the volume of fluid that occupies the path 904, the width of path 904 is narrower than the width of channel 902. When a second access port 906 is proximate the first access port 900, it can be difficult to drill a hole to access one port without inadvertently drilling into the other access port. To minimize this risk, second access port 906 is staggered relatively to the first access port 900 by utilizing a second path 908 which has a length different from the length of path 904. In the embodiment depicted, path 908 is shorter than path 904. In a similar fashion, one can access fluid inlet 910 by drilling a hole in the layer to expose the fluid inlet 910 to the ambient environment.

In one embodiment, the first, second and third layers are formed of an optically transparent, biocompatible material to facilitate visual inspection of the cells as well as permit microscopic probing of the sample. Examples of suitable materials include polydimethylsiloxane (PDMS), poly (methyl methacrylate) and other similar materials. Advantageously, PDMS is hydrophobic (i.e. water-impermeable) and thus forms fluid-impermeable region 208 while permitting fluid flow through the nests of pores 112.

In one embodiment, the hydrogel is a peptide-based hydrogel sold under the brand name PURAMATRIX™. This hydrogel is an exemplary peptide-based hydrogel with over 99% water content that can self-assembly into 3D interweaving nanofibers after a salt solution is added. Such a hydrogel provides pore size ranges from about 50 nm to about 200 nm. The peptide sequence may be chosen to promote cell attachment and migration (e.g. peptide RAD16-I).

In the embodiments depicted, a select number of channels are shown. It should be understood that other embodiments may use more channels or fewer channels and that such embodiments are contemplated for use with the present invention. Additionally, the fluid inlets and fluid outlets are exchangeable. This permits a different number of drugs to be introduced. For example, two inlets may be used with eight outlets when two drugs are employed. As a further example, eight inlets with two outlets may be used when eight drugs are employed. The fluid inlets and fluid outlets are not necessarily at opposite ends of the cell array. Depending on the fluid pathway, the fluid inlet and/or fluid outlet may be positioned at another location.

An imaging method to detect dynamic signals from live cells cultured in the cellular array is may be used to monitor cell growth in real time. For example, fluorescence microscopy and z-direction slicing with a moving objective and an on-stage incubator may be used. Suitable equipment is commercially available and includes the AxioObserver Z1 by Zeiss, Inc. Deconvolution software may be used to generate clear 3D cell images from z-stack images. The system described herein permits real time drug mechanism studies, including drug kinetics with spatial resolutions in apoptotic signaling networks using a scalable 3D microfluidic platform.

Figure 10:
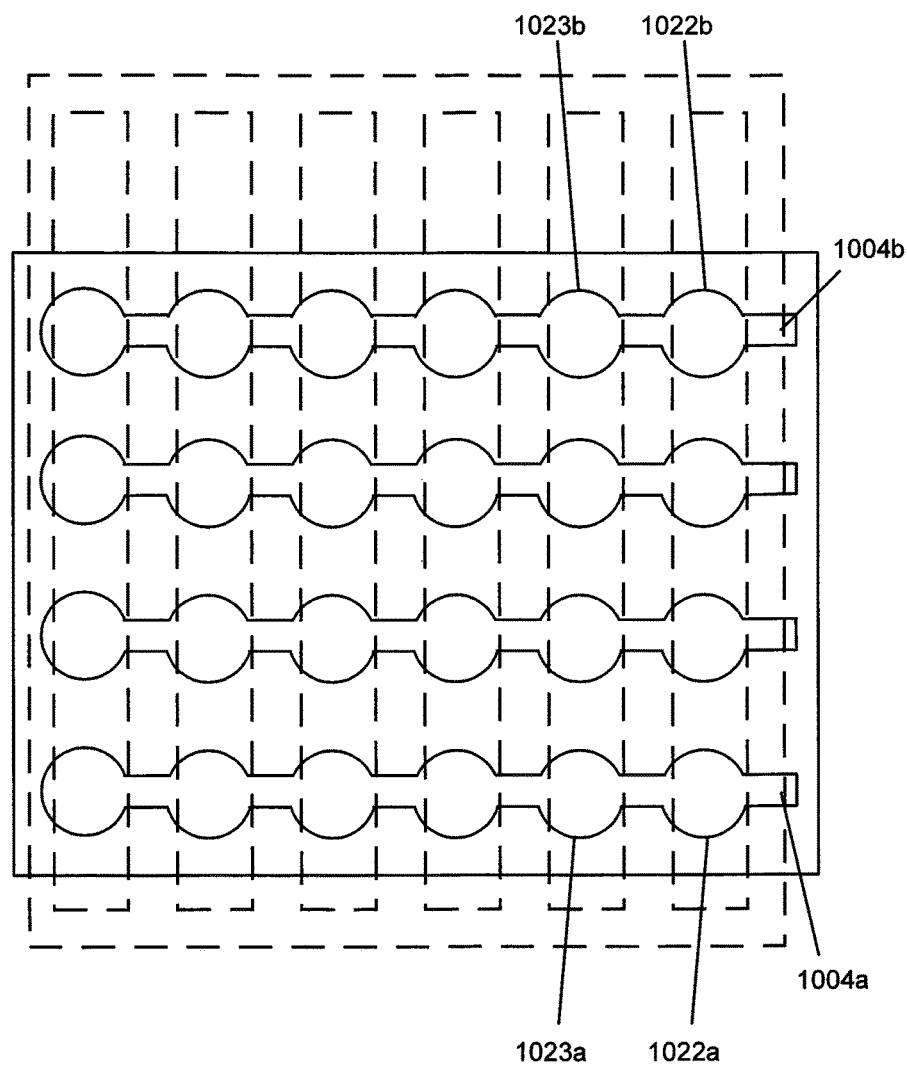
FIG. 10 is a schematic view of an exemplary first layer used in a combinatorial drug screening process.

Referring to FIG. 10, in one embodiment, the cell array is used in a combinatorial drug screening process. A variety of cellular samples may be placed in a cell array in which each sample is disposed in its own cell culture chamber to form rows. For example, a first type of cancer cell may be placed in first cell culture chambers 1022a, 1023a while a second type of cancer cell is placed in second cell culture chambers 1022b, 1023b. A select drug is screened by sending the drug, at a predetermined concentration, through a microfluidic channel. For example, a first drug is introduced into the array such that it contacts cell culture channel 1004a while a second drug is introduced into the array such that it contacts cell culture channel 1004b. In the embodiment of FIG. 10, the first layer and the second layer are orthogonal with the second layer shown in phantom. Because the rows of cancer cell types are orthogonal to the longitudinal direction of the cell culture channels, a wide variety of drugs can be screened against multiple cancer cell types. In one embodiment, microvalves are positioned in the cell culture channel between each of the cell culture chambers. The microvalves prevent two different drugs from cross contaminating the cell culture chambers. Suitable microvalves are known. See, for example, an article entitled "A high-throughput microfluidic real-time gene expression living cell array" by King et al. (Lab Chip; 2007 January; 7(1) 77-75). When the bottom layer is seeded with cells, the valves may be opened. After seeding, the valves may be closed. One of the microfluidic channels may be a drug-free fluid to function as a control.

One advantage of the technique described above is the ability of the system to microscopically monitor cell growth in real time as the cell culture develops. In one embodiment, the microscopic data is subjected to data mining to permit the screening process to be automated. Another advantage is the capability of using the cell array in personalized medicine. Tumor cells, and/or other types of cells, from a particular patient may be quickly subjected to a wide variety of drugs so that the most effective drug for that individual can be quickly identified.

Figure 11:
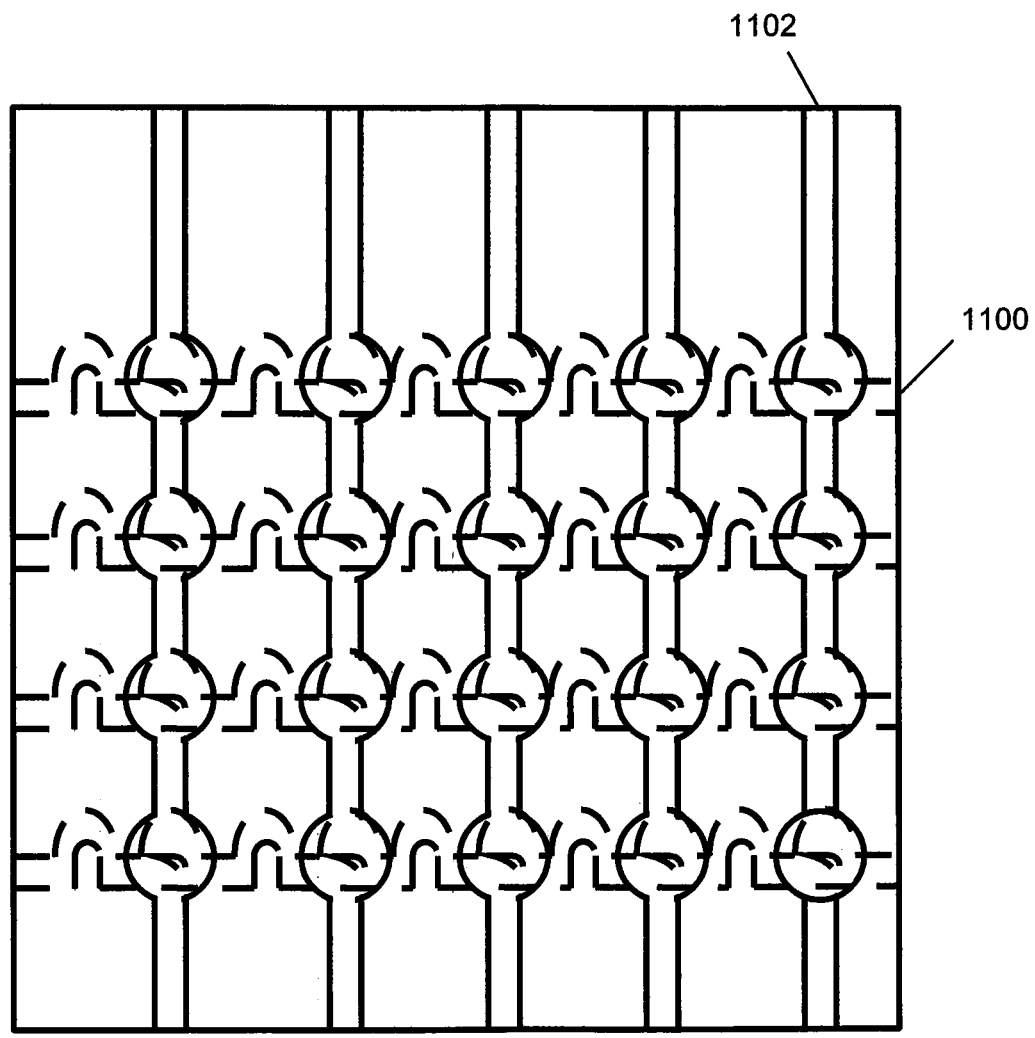
FIG. 11 is a schematic view of a tissue array used in a drug screening process.

FIG. 11 depicts another array for use in drug screening using tissue samples. The array of FIG. 11 comprises a first layer 1100, which is shown in phantom, disposed under a second layer 1102. The integrated architecture of the array, coupled with flow control, permits a user to catch and culture tissue samples in an array format. The array simulates an in vivo tissue environment including flow condition and transport scenario. For clarity of illustration, each of these layers are illustrated separately in FIG. 12 and FIG. 13 with the third layer being omitted.

Figure 12:
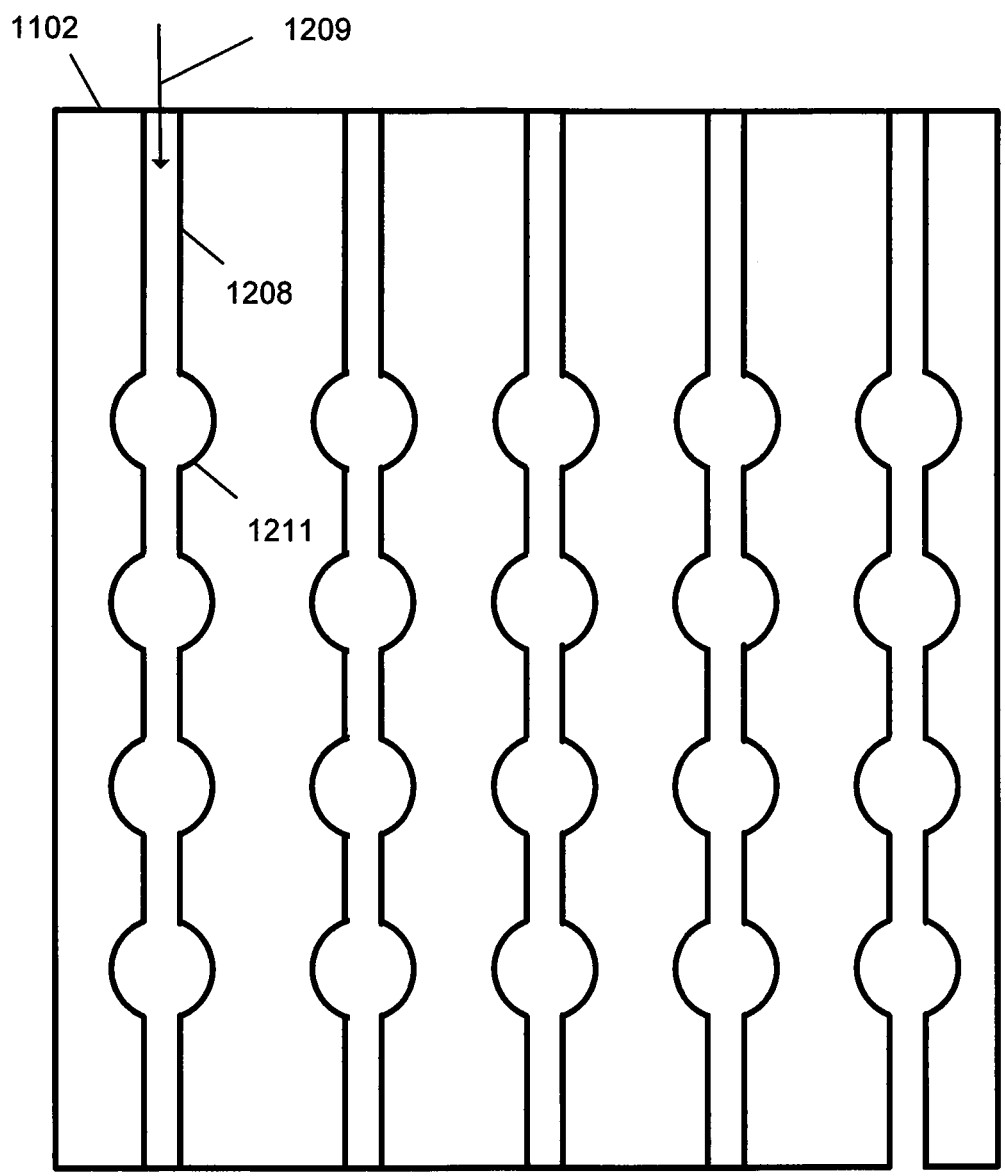
FIG. 12 is schematic view of a second layer of the array of FIG. 11.

FIG. 12 depicts the second layer 1102. The second layer 1102 comprises a plurality of microfluidic channels 1208. Liquid media may be passed through the microfluidic channels 1208 in, for example, the direction of arrow 1209. The liquid media may contain, for example, a drug at a predetermined concentration with different drugs being sent through different microfluidic channels. At multiple positions along the length of a given microfluidic channel 1208, the width of the microfluidic channel widens and thereafter narrows to form media reservoirs 1211. Each media reservoir 1211 is vertically aligned with a nest of pores similar to the nest of pores 112. The nest of pores provides fluid communication between the media reservoir 1211 and a corresponding culture chamber in the first layer 1100 (see FIG. 13).

Figure 13:
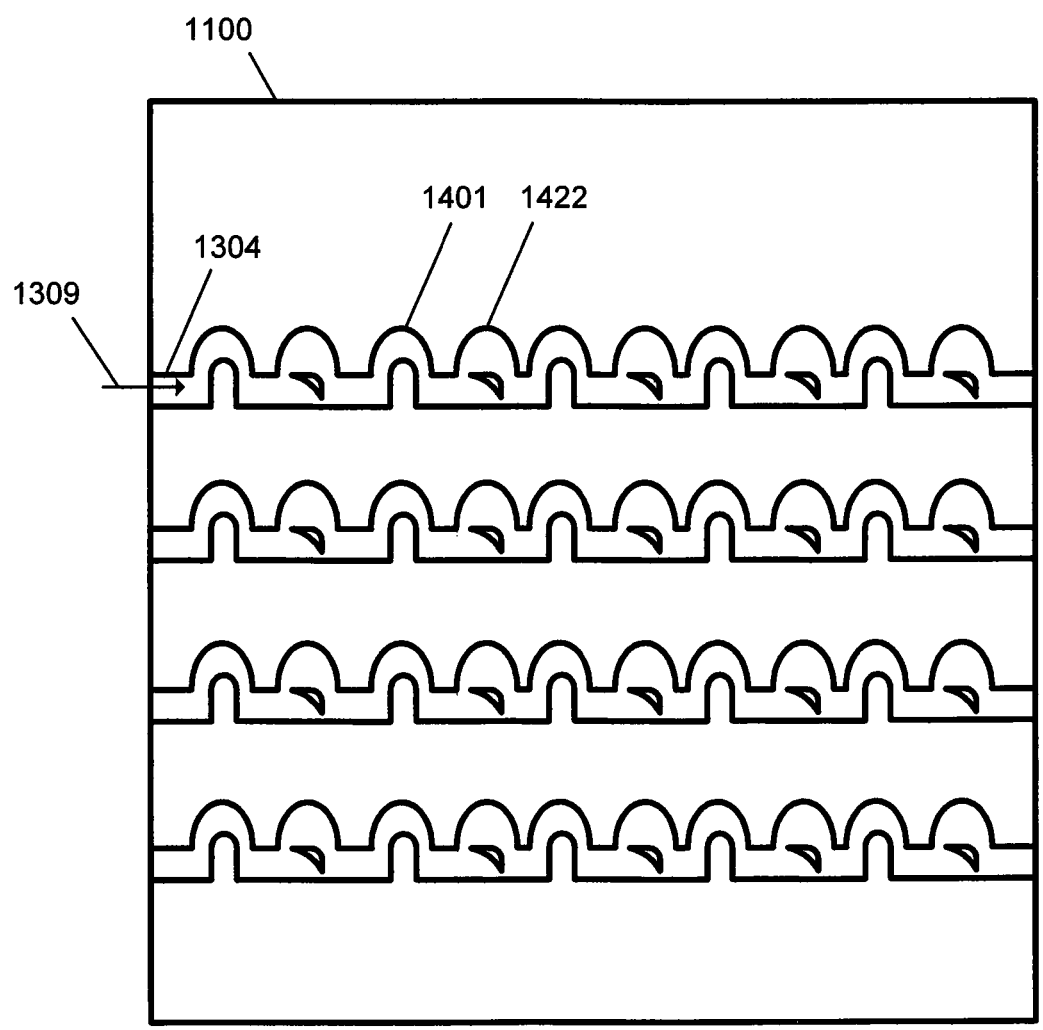
FIG. 13 is a schematic view of a first layer of the array of FIG. 11.

FIG. 13 depicts the first layer 1100. The first layer 1100 comprises a plurality of culture channels 1304 which are orthogonal to the microfluidic channels 1208 of the second layer 1102. Fluid flow occurs in the direction of arrow 1309. Each culture channel 1304 comprises a plurality of culture chambers 1422, each of which is disposed downstream of a curved path 1401. A more detailed view is provided in FIG. 14.

Figure 14:
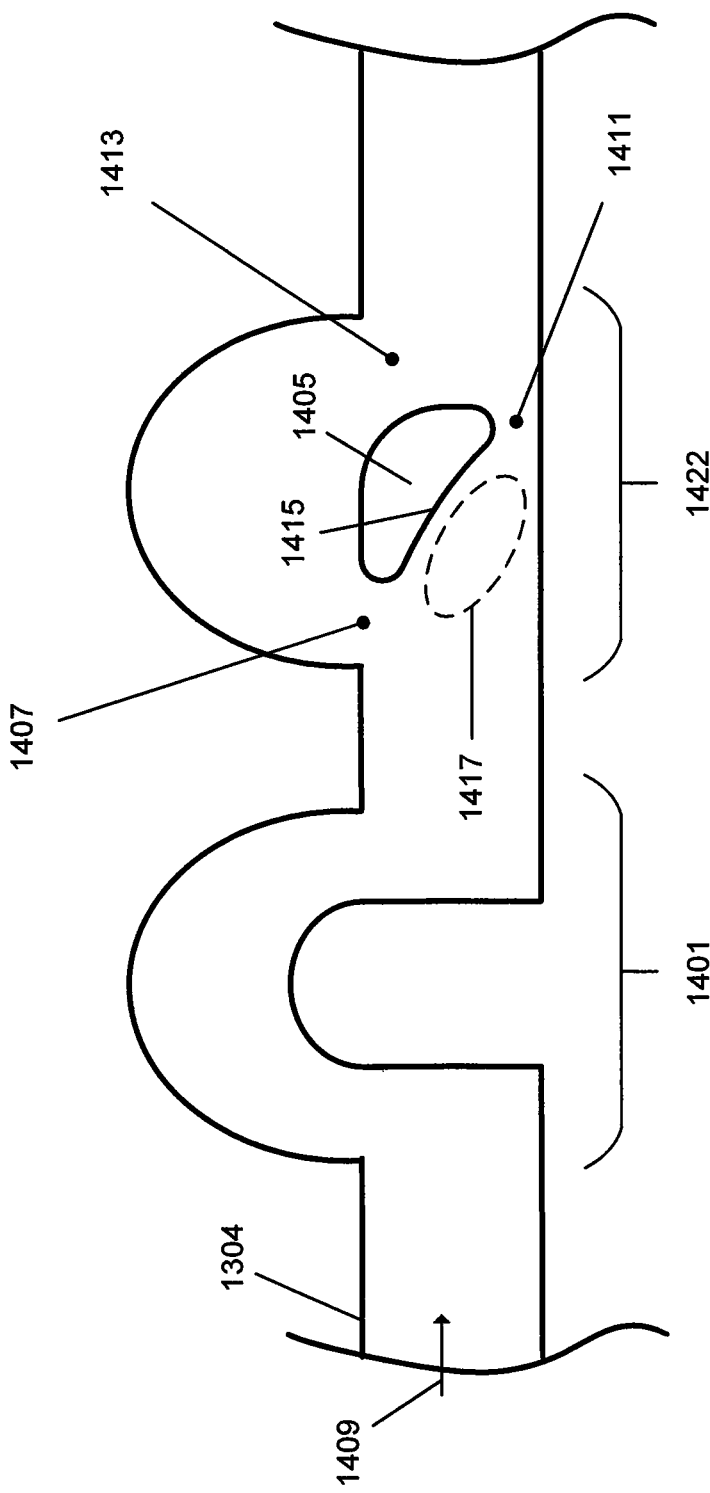
FIG. 14 is a magnified view of a trap of a culture channel in the first layer of the array of FIG. 11.
Figure 15:
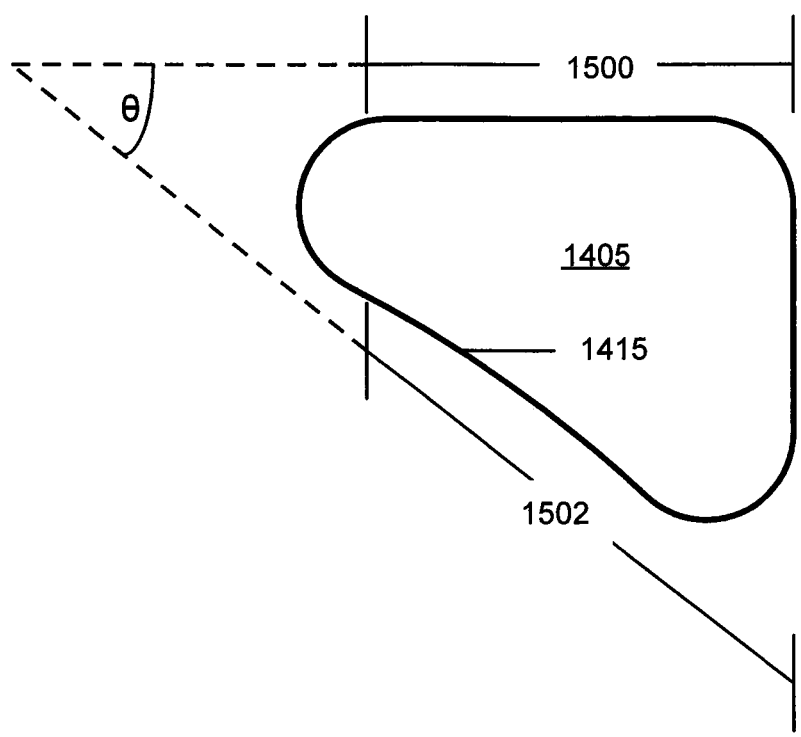
FIG. 15 is a magnified view of a fluid diverter of the culture channel of FIG. 14.

FIG. 14 illustrates an enlarged view of a trap that comprises the culture chamber 1422 and the curved path 1401. Fluid enters the culture channel 1304 in the direction of arrow 1409. In one embodiment, the fluid comprises a hydrogel-encapsulated-cell sample or a tissue sample. As fluid enters the culture channel 1304 the fluid encounters the curved path 1401 and fluid's momentum, and the momentum of any sample within the fluid, is reduced by the curvature. After exiting the curved path 1401 the fluid encounters a fluid diverter 1405 that diverts the fluid into two path through a bypass opening 1407 and a flow-through opening 1411. The flow-through opening 1411 permits fluid flow in a direction that is parallel to the longitudinal direction of the culture channel 1304. The flow-through opening 1411 has a diameter between about 10% to about 50% of the width of the culture channel 1304. The bypass opening permits fluid flow in a direction that is perpendicular to the longitudinal direction of the culture channel 1304 and thereafter unifies the fluid with the culture channel 1304 at a unification opening 1413. The fluid diverter 1405 comprises an angled wall 1415 that defines the width of the flow-through opening 1411. As shown in FIG. 15, the fluid diverter 1405 has a length 1500 that extends parallel to the longitudinal direction of the culture channel 1304. The angled wall 1415 has a length 1502 that is offset from the length 1500 by an angle θ such that the width of the culture channel 1304 gradually changes until finally reaching a minimum width at flow-through opening 1411. The angled wall 1415 may be a flat wall or a curved wall.

The configuration of the tissue array is configured to control fluid velocity and oxygen mass fraction within the array. The fluid velocity within the curved path is generally lower than the fluid velocity through the bypass opening. For example, the fluid velocity in the curved path may be about $1\times10^{-8}$ meters per second and the fluid velocity in bypass opening is within one order of magnitude of $1\times10^{-6}$ meters per second. The fluid velocity around the tissue is generally maintained between 0.1 μm per second and 10 μm per second. The oxygen mass fraction is generally higher in the curved path than in the bypass opening. For example, the if mass fraction of oxygen in the curved path is at 100% saturation, the mass fraction of oxygen in the bypass opening is about 85-90%. The mass fraction of oxygen in the flow-through opening may be about 70-90%. Such a configuration has been successfully used to maintain xenograft tissue in a high viability state for over a week.

As shown in FIG. 14, this configuration promotes entrapment of samples 1417 (e.g. a cell sample or a tissue sample). The first layer 1100 serves as a channel through which tissue pieces at millimeter scale are passed to be entrapped in the "catchers" (traps) designed specifically for the expected size of tissue pieces. Once the tissue pieces are caught and lodged into the catchers, media appropriate to the tissue sample can be passed in from the second layer 1102. The directional flow changes caused by the curved path 1401 and the angled wall 1415 further facilitates the tissue pieces staying within the catcher without risk of being flushed out. The flow from the second layer 1102 is not fully perceived by the tissue pieces lodged in the first layer 1100. Instead, the flow from the second layer 1102 trickles in through the third layer, wherein each culture chamber 1422 ("catcher" domain) is interfaced by precisely positioned pores. In the tissue array, the pores have a diameter between 40 μm and 500 μm and the microchannels of the first layer 1100 have a width between 500 μm to 2 millimeters such that tissues can travel through the microchannels. In one embodiment, the pores have a diameter between 10 micrometers and 500 micrometers. In one embodiment, the pore diameter is between 40 μm and 100 μm and the microchannel width is between 1 mm and 2 mm. In one embodiment, the microfluidic channel has a width between 100 micrometers and 2 millimeters. The pore diameter, the number of pores and their positions are optimized depending on the desired flow conditions around the tissue, as determined by computational fluid dynamics. This architecture allows for modulation of both the flow direction to keep the tissue in place, as well as flow magnitude to match the necessary needs, such as nutrient supply or adequate shear/flow conditions to simulate tissue interstitial flow and/or capillary flow around tissues.

In one embodiment a system ("3D Microfluidic Tissue Lab") is provided that comprises a tissue array, an incubator, a pump system that controls medium and compound perfusion rates, an enclosed microscope and a computer controller that controls the pump, gathers and processed 3D data from the sample. Many conventional 3D cell culture systems partially replicate the in vivo environment, but fall short by not including a mimicked micro-vascular circulation mechanism with a reasonable throughput. The disclosed 3D microfluidic cell array (μFCA) and microfluidic tissue array (μFTA) address this need.

When cancer patients' own biopsy samples are tested against multiple potential therapeutic drugs using the disclosed "3D Microfluidic Tissue Lab" before oncologists prescribe their first treatment, not only are the cancer patients are no longer the subject of the drug test, but the patients can also be treated with the most effective and personalized medicine initially. With its ability to mimic the cellular environment of a tumor in a human body, the disclosed technology provides accurate results to the clinicians and gives insight concerning how an individual patient's cancer will respond to a specific drug regime.

The disclosed 3D Microfluidic Tissue Lab can host different types of tissue samples (e.g. xenograft human tumors, patient-derived xenograft tumors or biopsy samples) and allows applying multiple drug/compound stimuli on the same chip. Using tissue samples enables biomedical researchers and pharmaceutical industry to perform ex vivo target discovery and drug development in native tissue microenvironment. Thus, the disclosed system facilitates screening and discovery of novel potential anti-cancer agents and clinical searching for personalized precision medicine for patients individually when patients' own biopsy tissues are used.

The layers described in this specification may be formed according to conventional microfabrication techniques. Such techniques are employed in the field of micro-electro-mechanical systems (MEMS). For example, a silicon wafer may be coated with a layer of photoresist. A patterned mask is used to selectively protect those areas of the wafer which will be the channels or pores. Treatment with ultraviolet light etches those areas not protected by the mask to produce a master mold. The master mold is coated with a polymerizable mixture. Upon polymerization, the layers are formed with the appropriate patters or pores and separated from the mold. Advantageously, such fabrication techniques permit the different layers to be formed as a single, monolithic structure which obviates leaks between the layers.

While the invention has been described with reference to certain embodiments, it will be understood by those skilled in the art that various changes may be made and equivalents may be substituted for elements thereof to adapt to particular situations without departing from the scope of the disclosure. Therefore, it is intended that the claims not be limited to the particular embodiments disclosed, but that the claims will include all embodiments falling within the scope and spirit of the appended claims.

Example 1

The device was tested by using food dyes. Liquid food dyes were introduced to the fluid inlets of the second layer with syringes. The flow with food colors moved through microfluidic channels and at the same time the dye diffused from the second layer to the first layer by passing through the pores on the third layer in 2.5 seconds. The diffusion time was estimated using a video capturing the complete procedure of the food color experiment.

Example 2

PC9 (non-small lung cancer) cells encapsulated in peptide hydrogel were cultured in the first layer for seven days. On day seven, calcein AM was introduced in the second layer to test the diffusion of the dye and viability of the cells. Live cells should be fluorescent green. Microscopic inspection showed that diffusion of calcein AM happens in seconds, and by fifty-two seconds all live cells become fluorescent green.

Example 3

A long term 3D cell culture for two weeks was also performed. PC9 cells were dyed with long term green fluorescent cell tracker and encapsulated in peptide hydrogel. A syringe pump was used to deliver fresh medium continuously at 0.5 microliters per minute in the second layer. Cells were imaged using an 10× objective with z-direction moving ability. Then a 3D image was reconstructed using z-stack images after deconvolution showing live cells.

Example 4

In order to show our device is feasible to perform a structured co-culture between cancer cells and endothelial cells, PC9 were dyed with red fluorescence cell tracker (DIL), seeded and cultured in the first layer for several days, followed by microvascular endothelial cell seeding in the second layer without dye. Microscopic inspection showed that a structured co-culture was achieved successfully. This experiment confirmed that not only micro-tumor arrays can be generated but that tumor microenvironments can also be mimicked that are similar to their in vivo conditions (e.g. tumors are surrounded by blood vessels without lymph vessels).

What is claimed is:

1. A layered, microfluidic array, comprising:
   a first layer comprising a plurality of culture channels extending in a first longitudinal direction, each culture channel having a plurality of traps, each trap comprising (1) a curved path and (2) a culture chamber disposed downstream, and spaced from, the curved path, each culture chamber comprising a fluid diverter that diverts fluid into a bypass opening and a flow-through opening, the fluid diverter comprising a first wall that extends parallel to the first longitudinal direction and an angled wall, the angled wall being offset from the first wall by an acute angle θ, wherein the fluid diverter, the bypass opening and the flow-through opening are all within a perimeter of the culture chamber;
   a second layer comprising a plurality of microfluidic channels extending in a second longitudinal direction, wherein the first longitudinal direction and the second longitudinal direction are orthogonal;
   a third layer, disposed between the first layer and the second layer, the third layer comprising pores grouped into a plurality of nests, each nest horizontally arranged within the third layer such that each nest is vertically stacked above, and fluidly connected with, a corresponding culture chamber in the first layer, each nest fluidly isolated from adjacent nests by a fluid impermeable region of the third layer such that horizontal diffusion of water within the third layer is prevented;
   a fluid inlet connected to a first end of the plurality of microfluidic channels; and
   a fluid outlet connected to a second end of the plurality of microfluidic channels.

2. The layered, microfluidic array as recited in claim 1, wherein each pore has a diameter between 10 micrometers and 500 micrometers.

3. The layered, microfluidic array as recited in claim 1, wherein each microfluidic channel in the plurality of microfluidic channels has a width between 100 micrometers and 2 millimeters.

4. The layered, microfluidic array as recited in claim 1, wherein the first layer, the second layer and the third layer are formed of an optically transparent material.

5. The layered, microfluidic array as recited in claim 1, wherein the first layer, the second layer and the third layer are formed of a transparent, biocompatible material.

6. The layered, microfluidic array as recited in claim 5, wherein the transparent, biocompatible material is polydimethylsiloxane (PDMS).

7. The layered, microfluidic array as recited in claim 5, wherein the transparent, biocompatible material is poly (methyl methacrylate).

8. The layered, microfluidic array as recited in claim 1, wherein the first layer has a first thickness, the second layer has a second thickness, and the third layer has a third thickness, wherein the first thickness and the second thickness are each greater than the third thickness.

9. The layered, microfluidic array as recited in claim 8, wherein the first thickness and the second thickness are between 60 micrometers and 1 millimeter each.

10. The layered, microfluidic array as recited in claim 1, wherein the layered, microfluidic array further comprising a first access port disposed at a terminus of a first channel.

11. The layered, microfluidic array as recited in claim 10, wherein the first channel is a culture channel in the plurality of culture channels.

12. The layered, microfluidic array as recited in claim 10, wherein the first channel is a microfluidic channel in the plurality of microfluidic channels.

13. A layered, microfluidic array, comprising:
   a first layer comprising a plurality of culture channels extending in a first longitudinal direction, each culture channel having a plurality of traps, each trap comprising (1) a curved path and (2) a culture chamber disposed downstream, and spaced from, the curved path, each culture chamber comprising a fluid diverter that diverts fluid into a bypass opening and a flow-through opening, wherein the fluid diverter, the bypass opening and the flow-through opening are all within a perimeter of the culture chamber, the fluid diverter comprising a first wall that extends parallel to the first longitudinal direction and an angled wall, the angled wall being offset from the first wall by an acute angle θ;
   a biological sample disposed within at least one trap of the plurality of traps;
   a second layer comprising a plurality of microfluidic channels extending in a second longitudinal direction, wherein the first longitudinal direction and the second longitudinal direction are orthogonal;
   a third layer, disposed between the first layer and the second layer, the third layer comprising pores grouped into a plurality of nests, each nest horizontally arranged within the third layer such that each nest is vertically stacked above, and fluidly connected with, a corresponding culture chamber in the first layer, each nest fluidly isolated from adjacent nests by a fluid impermeable region of the third layer such that horizontal diffusion of water within the third layer is prevented;
   a fluid inlet connected to a first end of the plurality of microfluidic channels; and a fluid outlet connected to a second end of the plurality of microfluidic channels.

14. The layered, microfluidic array as recited in claim 13, wherein the biological sample is a cellular sample.

15. The layered, microfluidic array as recited in claim 13, wherein the biological sample is a tissue sample.

16. A method for capturing a biological sample, the method comprising a step of:
  passing a mixture of a fluid and a biological sample into the layered, microfluidic array as recited in claim 1, such that the fluid passes through the plurality of culture channels of the first layer;
  wherein the curved path interrupts flow of the fluid along the first longitudinal direction such that momentum of the fluid is reduced relative to momentum of the fluid before the curved path.

17. The method as recited in claim 16, wherein the fluid has a first velocity through the curved path and a second velocity through the bypass opening, the first velocity being lower than the second velocity.

18. A method for culturing a biological sample, the method comprising a step of:
  passing a liquid medium into the layered, microfluidic array as recited in claim 13, such that the liquid medium passes through the plurality of microfluidic channels of the second layer, and passes into the plurality of culture channels of the first layer through the pores of the third layer.

* * * * *